United States Patent [19]
Mikhail et al.

[11] Patent Number: 5,171,288
[45] Date of Patent: Dec. 15, 1992

[54] FEMORAL STEM PROSTHESIS WITH PREAPPLIED CEMENT MANTLE

[76] Inventors: W. E. Michael Mikhail, 4203 Shamley Green, Toledo, Ohio 43623; James J. Elting, 35 Academy St., Oneonta, N.Y. 13620

[21] Appl. No.: 673,367

[22] Filed: Mar. 22, 1991

Related U.S. Application Data

[63] Continuation-in-part of Ser. No. 577,027, Sep. 4, 1990, Pat. No. 5,080,680.

[51] Int. Cl.⁵ .............................................. A61F 2/34
[52] U.S. Cl. ........................................ 623/23; 623/16; 623/18
[58] Field of Search ................. 623/16, 18, 20, 22, 623/23

[56] References Cited

U.S. PATENT DOCUMENTS

| | | | |
|---|---|---|---|
| 3,793,650 | 2/1974 | Ling | 623/23 |
| 3,986,212 | 10/1976 | Sauer | 623/16 |
| 4,281,420 | 8/1987 | Raab | 623/16 |
| 4,491,987 | 1/1985 | Park | 623/23 |
| 4,619,659 | 10/1986 | Witzel | 623/16 |
| 4,851,004 | 7/1989 | Homsy | 623/18 |
| 4,904,267 | 2/1990 | Bruce et al. | 623/16 |

FOREIGN PATENT DOCUMENTS 0243585 11/1987 European Pat. Off. ............. 623/23

*Primary Examiner*—David Isabella
*Attorney, Agent, or Firm*—Emch, Schaffer, Schaub & Porcello Co.

[57] ABSTRACT

A femoral stem prosthesis has a first structural collarless component formed of a highly polished metal, double tapered stem extending from a distal end to an enlarged shoulder and a neck and a second component comprising preapplied cement mantle having a thickness in the range of 0.75 to 2 mm extending intermittently throughout a major portion of said stem.

15 Claims, 4 Drawing Sheets

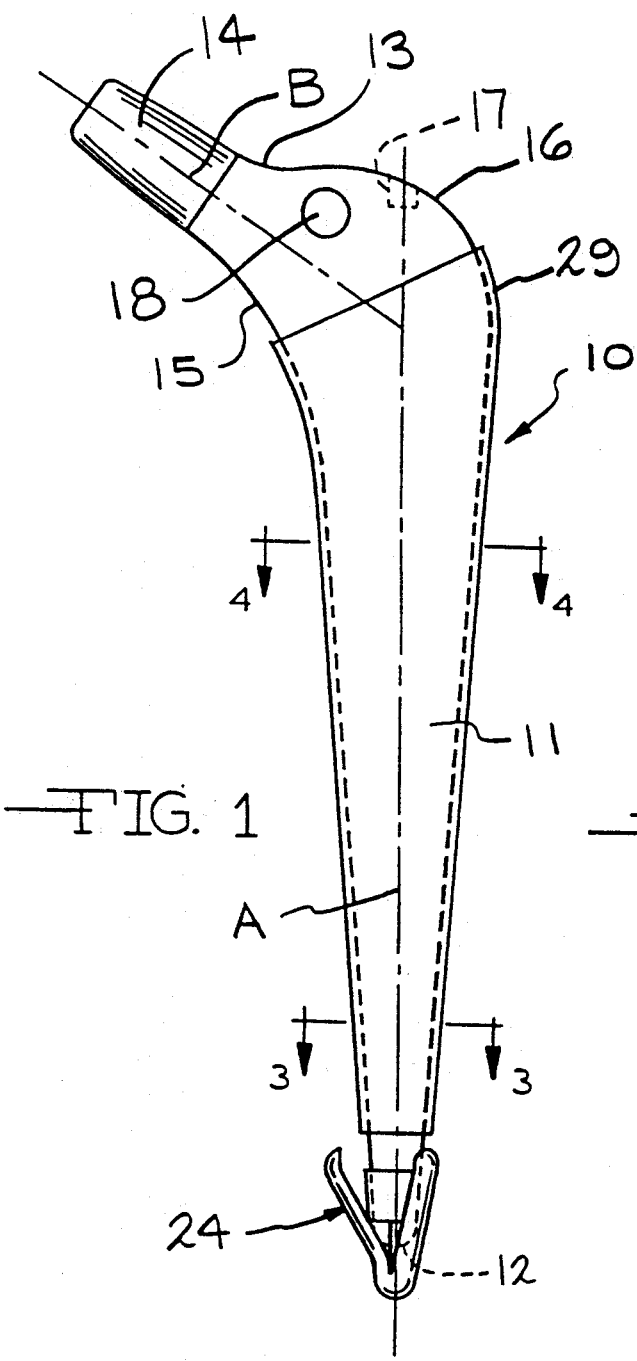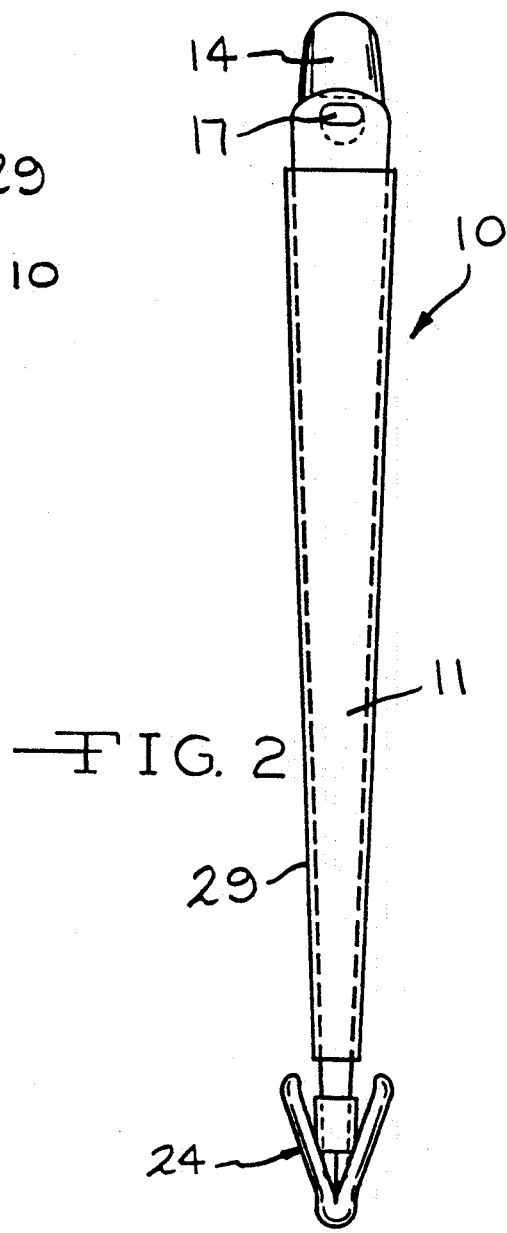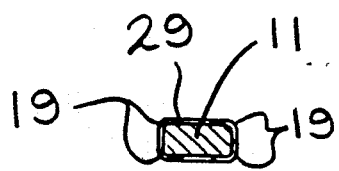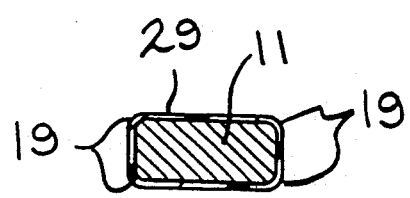

FEMORAL STEM PROSTHESIS WITH PREAPPLIED CEMENT MANTLE

CROSS REFERENCE TO RELATED APPLICATION

This application is a continuation-in-part of application Ser. No. 07/577,027, filed Sep. 4, 1990, now U.S. Pat. No. 5,080,680.

BACKGROUND OF THE INVENTION

The present invention relates to a hip joint prosthesis and more particularly to the femoral component of such a prosthesis.

Many methods and devices have been developed to improve the fixation of hip joint prostheses including the femoral component thereof in the body so that the device implanted therein becomes as permanent as possible. Many orthopeadic implants use a cement to anchor the stem portion of a femoral component in the femur. For example, United Kingdom Patent Specification No. 1,409,054 in the names of Robin S. M. Ling (one of the co-inventors of the present application) and Alan J. C. Lee (incorporated herein by reference) discloses a hip joint prosthesis having a double-tapered stem which, among other advantages, enhances extrusion of cement caused by penetration of the stem during fixation. U.S. Pat. No. 3,793,650 (incorporated herein by reference) one of the co-inventors of which is also Robin S. M. Ling, discloses an intramedullary stem for a prosthetic bone joint device having a base with spring members intended to centralize the position of the stem in the canal or bore of the bone in order to insure a relatively uniform or, at least minimum, thickness of cement between the wall of the bone and the stem. It is desirable that there be at least two millimeters (2 mm) of cement between the stem and the bone. By providing a means for insuring that there will be at least a certain minimum thickness of cement between the stem of the prosthesis and the interior wall of the canal formed in the femur bone for receiving such stem, the likelihood of the stem protruding through the cement and contracting the interior of the femur bone itself is minimized. Thus, in those types of implants using cement, it is important to insure that the stem is completely encapsulated by the cement and does not protrude through to contact the bone.

One type of bone cement utilized to retain the stem of a femoral hip joint prosthesis in the canal of a bone comprises a mixture of polymethylmethacrylate (hereinafter PMMA) polymer and methyl methacrylate monomer and optionally including a styrene co-polymer of PMMA. This and other types of cement utilized for such purpose may be packaged in two separate components which are mixed into a paste which is placed in the canal of the femur immediately prior to insertion of the stem of the prosthesis. Such paste then sets to a relatively rigid material providing excellent adherence to the interior wall of the bone. Some prior art femoral stem prostheses have utilized a precoating of a film of PMMA cement. Prostheses having a film of PMMA or other type of bone cement coated thereon prior to implantation are disclosed in the following U.S. Pat. Nos. 4,281,420; 4,336,618 and 4,491,987 (incorporated herein by reference).

Prior to the invention disclosed in our co-pending application Ser. No. 07/527,298 filed May 23, 1990, it had been the belief that it is desirable to have good adhesion between the stem and the cement. Many prior art devices were specifically directed to providing a design for the prosthesis intended to maximize adhesion between it and the cement. This has been true of ones utilizing a precoating as well as ones in which the stem has a bare metallic surface which comes into direct contact with PMMA or other bone cement deposited in the medullary canal of the femur.

In U.S. Pat. No. 4,281,420 and its divisional U.S. Pat. No. 4,336,618, which relate to prostheses utilizing a precoating of film of PMMA, it is pointed out that those inventions are directed towards "prostheses adapted to maximize strength and durability of the prostheses/bone cement adherence". (See "Field of the Invention" for both of the above patents). These inventions are specifically directed to a procedure and device for maximizing the strength of the interface between the prosthesis and the bone cement through the use of a film coating of PMMA having a thickness which may be as thin as 0.0001 inch and preferably is about 0.0002 inch.

U.S. Pat. No. 4,491,987 states as one of the objects that the invention described and claimed therein "improves the interfacial bond between the prosthesis and the bone tissue to which it is affixed." (See column 2, lines 66–68). Under the teachings of that patent, the prosthesis is precoated with a polymer layer that is compatible with the bone cement utilized during surgical implantation and has a maximum thickness controlled only by the size of the bone cavity. The purpose of such layer is to ". . . achieve a structurally sound bond therebetween." The specification goes on to state that "the surface of the prosthesis to receive the polymer coating should be pretreated immediately prior to application of the coating to roughen or otherwise prepare the surface to achieve a structurally sound bond at the prosthesis coating interface." (See column 3, lines 31–36). This patent also explained the great advantages of utilizing a prosthesis having a roughened surface in order to obtain greater "interfacial implant-precoat maximum stress." (See column 9, lines 15–16).

Examples of non-coated prostheses include the CML Cemented Medullary Locking Hip System manufactured by DePuy Division of Boehringer Mannheim Corporation, Warsaw, Ind., which is a hip system in which the upper portion of the stem is provided with a roughened textured surface intended to enhance the bond of the cement to the prosthesis at the prosthetic interface. It also utilizes a "Macro-Textured" waffle design which is intended to increase the surface area and the mechanical interlock between the cement and the prothesis in the area of such waffle design.

Osteonics Corp., Allendale, N.J., manufactures the OMNIFLEX Femoral System of a titanium alloy having a normalized surface to promote good adhesion of the cement thereto.

Other types of devices which disclose the use of cement within a bore or canal of the femur are described in U.S. Pat. Nos. 3,829,904; 3,874,003; 4,012,796 and 4,080,666. The disclosures of the aforesaid patents are hereby incorporated by reference. Copies of such patents are enclosed.

In cemented types of devices used heretofore, both those having PMMA or other types of precoatings and those without any such precoating, problems have arisen, particularly after a number of years of implantation. Problems have also arisen with femoral hip joint prostheses which do not utilize any bone cement for implantation. With respect to the cemented type devices, part of the problem arises from the fact that the cement utilized to retain the stem of the device in the canal of the femur bone is subject to a phenomenon known as creep. Thus, while the bone cement appears to be rigid when set, it is subject to minute amounts of movement over time. The amount of creep encountered with such cement following implantation is exaggerated by virtue of the fact that the body temperature controls the temperature of the implanted cement and prosthesis. Thus, PMMA and other types of bone cement at body temperature are subject to a greater degree of creep than bone cement maintained at room temperature of, say, 72° F. This may be readily observed by mounting a bar of PMMA so that its ends are supported and applying a fixed load at the center of the bar. Tests have shown that a bar so supported and subjected to a load of 5 pounds for eight hours at 98.6° F. will deflect to an extent 3.5 times greater than an identical bar supported and loaded in an identical manner for eight hours at 72° F.

Over a period of time, the phenomenon of creep may result in disruption of the micro-interlocking of the cement-bone interface, especially if the cement mantle is firmly bonded to the femoral prosthesis. As is well known in the field of hip replacements, it is important that there be a good bond between the cement and the bone and that there be no disruption in the micro-interlocking of the cement-bone interface.

Subsidence of the femoral component occurs in various degrees with prostheses of different designs regardless of the presence or absence of collars. Any prosthesis which is firmly bonded or fixed to the cement will, upon subsidence, disrupt the cement bone interface and inevitably lead to clinical loosening and subsequent failure necessitating revision. The presence of a collar may cause the stem of the prosthesis to go into varus during any such subsidence.

SUMMARY OF THE INVENTION

The present invention relates to a femoral hip joint prosthesis having a preapplied cement mantle having a thickness in the range of 0.75 to 2.0 millimeters (0.75 to 2.0 mm) and preapplied over a tapered collarless polished stem which allows subsidence of the stem within the cement mantle without disrupting the micro-interlocking in the interface between cement and the bone following implantation in a prepared canal having additional cement placed therein. Upon insertion of the prosthesis into the femoral canal in which additional cement has been placed, the preapplied cement mantle joins with and becomes integrally connected to such additional cement to hold the prosthesis in the proper position. The absence of a collar permits any subsidence of the prosthesis to occur substantially along the axis of the stem and prevents the stem from going into varus during the occurrence of any such subsidence.

Application Ser. No. 07/527,298 filed May 23, 1990 by two of the Applicants herein is directed to a Femoral Stem Prosthesis having a similar shape as that of the present invention but with no preapplied cement mantle. The present invention is a further improvement over the Femoral Stem Prosthesis described and claimed in application Ser. No. 07/527,298 filed May 23, 1990. The utilization of the preapplied cement mantle in combination with the tapered collarless polished stem formed of a chrome cobalt molybdenum alloy insures that there will be a sufficient thickness of cement between the bone tissue of the femoral canal and the metal component of the stem and also provides the advantages of a prosthesis which allows subsidence of the stem within the cement mantle without disrupting the micro-interlocking in the interface between the cement and the bone.

Accordingly, it is an object of the present invention to provide a new and novel femoral hip joint prosthesis which is specifically designed to insure a sufficient thickness of the cement mantle while avoiding the forementioned problems resulting from subsidence of the stem.

It is a further object of the present invention to provide a femoral hip joint prosthesis with a preapplied cement mantle which will not loosen but rather will self-tighten even though the cement mantle creeps or expands fractionally over a period of time.

It is yet another object of the present invention to provide a femoral hip joint prosthesis having a preapplied cement mantle which becomes joined with and an integral part of additional cement placed in the femoral canal upon implantation. Upon subsidence within the cement as the cement creeps the stem is permitted to remain at all times in snug interfacial contact with the cement thus imparting in the stem area the reliable compressive forces against the cement which is micro-interlocked with the bony surface.

It is another object of the present invention to provide a femoral hip joint prosthesis having a preapplied cement mantle implanted in a femoral canal having additional cement which self compensates and subsides within the cement mantle as such cement mantle creeps over time without disrupting the micro-interlocking and thus preserving the cement-bone interface.

The femoral hip joint prosthesis of the present invention is collarless, has a double tapered stem formed of cobalt chrome molybdenum alloy, has the surface of the stem highly polished to provide an extremely smooth surface which should not exceed maximum level of roughness and a preapplied cement mantle. The lower end of the stem is positioned in a hollow centralizer which serves both to stabilize it and as an additional means to insure that an adequate thickness of cement encapsulates the stem. Such design permits the stem portion of the prosthesis to move fractionally within the cement mantle without disrupting the cement-bone interface and to self-tighten as the male component, namely, the distal tip of the stem engages further in the hollow centralizer.

Under one embodiment, the preapplied cement mantle is applied intermittently over the stem to provide a series of interstices or openings through the preapplied cement mantle through which the polished surface of the stem is visible. Under this embodiment, upon insertion of the prosthesis into the femoral canal in which additional cement has been placed, such additional cement will not only join with and become integrally connected to the intermittently preapplied cement mantle, but will also flow into the interstices to engage the polished surface. This may enhance the integral connection between such additional cement and the preapplied cement mantle while still permitting subsidence of the stem within the cement mantle without disrupting the micro-interlocking in the interface between the cement and the bone. Additionally, under this embodiment, those portions of the additional cement which flows into the interstices will be thicker than those portions of such additional cement which is aligned with the preapplied cement mantle itself.

BRIEF DESCRIPTION OF THE DRAWINGS

FIG. 1 is a front elevational view of the femoral hip joint prosthesis, according to the present invention and a centralizer.

FIG. 2 is an end view of such femoral hip joint prosthesis.

FIG. 3 is a sectional view taken through line 3—3 of FIG. 1.

FIG. 4 is a sectional view taken through line 4—4 of FIG. 1.

DETAILED DESCRIPTION OF THE DRAWINGS

Figure 5:
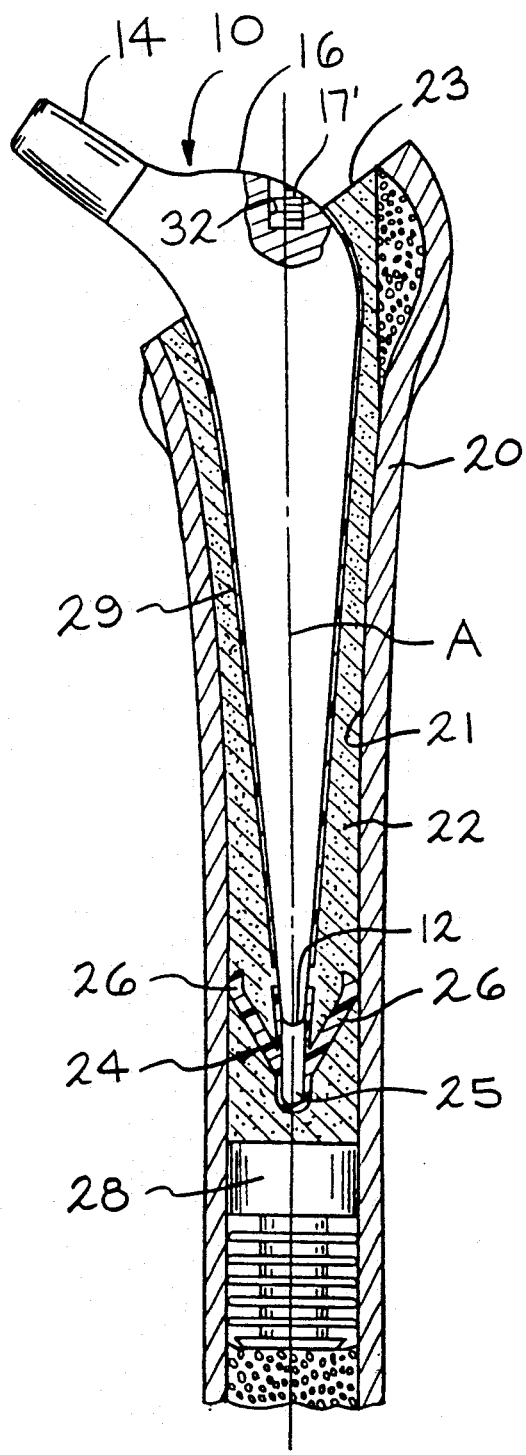
FIG. 5 is a sectional view showing the femoral hip joint prosthesis of the present invention immediately after implanting in a patient.

Referring now to FIGS. 1 and 2, there is shown a femoral hip joint prosthesis 10 having a stem 11 which is convergently tapered toward a distal end 12 and extending along a first axis of symmetry A to an area of juncture with a neck portion 13 lying on a second axis of symmetry B. Extending from the neck portion 13 is a frustoconically shaped Morse Taper Neck 14 to which may be attached a spherically shaped Morse Taper Head. As is clear from FIG. 1, no collar is provided in the femoral hip prosthesis, but rather the portion of the prosthesis joining the stem 11 to the neck 13 follows a smooth arcuate contour in the area 15 of the included angle between the respective axes of symmetry A and B. The portion of the femoral hip prosthesis 10 opposite the smooth arcuate portion 15, namely, that portion on the outside of the angle between the two axes of symmetry A and B, has an enlarged shoulder 16 in which is formed a dimple or recess 17 for driving the prosthesis into the femur. As can be seen, the dimple 17 is located on the first axis of symmetry A.

An aperture 18 is provided in the area of the neck and shoulder to assist in removing the prosthesis 10 in the event revision is required at some future time.

As can be seen in FIGS. 3 and 4, the stem 11 is tapered in both directions and has rounded corners 19. As pointed out in United Kingdom Patent Specification 1,409,054, such double tapering enhances the extrusion of cement caused by penetration of the stem 11 thereinto during fixation.

The femoral hip joint prosthesis further includes a preapplied cement mantle 29 of PMMA or other commercially available bone cement. The preapplied cement mantle 29 encapsulates almost all of the stem 11 up to the area of the smooth arcuate portion 15 and the beginning of the enlarged shoulder 16. For reasons which will become clear, in the preferred embodiment, there is no preapplied cement mantle above the distal end 12 to an area about one (1) centimeter upwardly therefrom. However, the distance between the distal end 12 and the beginning of the preapplied cement mantle could be in the range of 0.5 to 1.5 centimeters (cm). Preferably, the preapplied cement mantle 29 has a substantially uniform thickness with the thickness being at least seven tenths of a millimeter (0.7 mm) and no thicker than about two millimeters (2 mm). Such preapplied cement mantle 29 is allowed to become fully set so that the femoral hip joint prosthesis 10 including such preapplied cement mantle 29 may be packaged and shipped to hospitals.

A hollow centralizer 24 is provided and frictionally engaged to the tapered distal tip (12). As will become clear, if subsidence occurs, it will do so within the cement mantle 29 and the hollow centralizer 24.

Except for the preapplied cement mantle 29 portion thereof, the femoral hip joint prosthesis 10 of the present invention is formed of high-strength forged Co-Cr-Mo alloy (ASTM designation F-799) and has its surface polished to a high degree (also known as a color buff finish) to provide for a smoothness having a target surface roughness of four (4) microinches. It has greater fatigue strength, corrosion resistance and wear resistance than stainless steel. Additionally, it resists pitting and crevice corrosion in the body environment.

Referring now to FIG. 5, there is shown the femoral hip joint prosthesis 10 of the present invention immediately following its implantation in the femur bone 20. As is customary, the femur bone 20 is prepared by reaming a canal 21 into which PMMA or other suitable bone cement is introduced under pressure. Promptly after introduction of the bone cement into the canal 21 and before the cement has had an opportunity to set, the stem 11 of the femoral hip joint prosthesis 10 with its preapplied cement mantle 29 is inserted into the cement with the result that an outer cement mantle 22 is formed around the stem 11 and preapplied cement mantle 29. Any excess cement is wiped away leaving an exposed upper end 23.

Although for purposes of clarity the preapplied cement mantle 29 and the outer cement mantle 22 are sectioned differently, it should be understood that, following implantation of the hip joint prosthesis 10 into the cement in the canal 21, the cement of the preapplied cement mantle 29 and the cement of the outer cement mantle 22 will be merged into an integral unitary cement mantle.

The free or distal end 12 of the stem 11 is engaged in the hollow plastic centralizer 24 with the polished metal surface being in direct contact with the plastic of the centralizer 24. The plastic centralizer 24 includes a cup-shaped pocket 25 having a plurality, preferably 3 or 4, of integrally formed resilient arms 26 sized to engage the interior of the canal 21. Prior to introduction of cement in the canal, a cement restrictor 28 is position therein.

Figure 6:
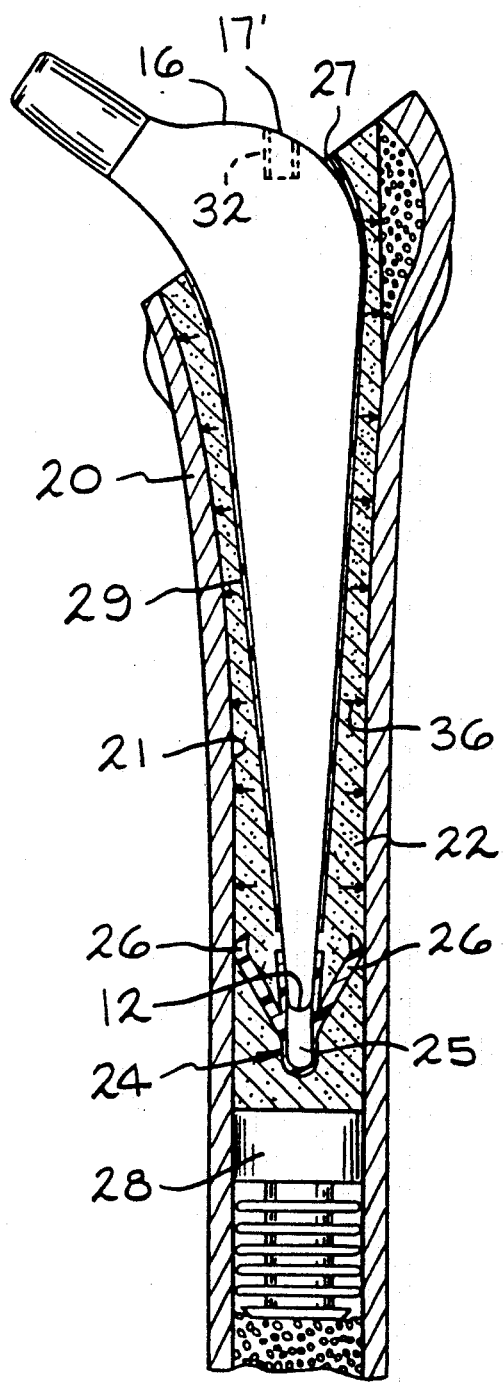
FIG. 6 is a view similar to FIG. 5 showing the femoral hip joint prosthesis after being implanted for a number of years and showing, greatly exaggerated, the effects of subsidence.

FIG. 6 shows the implanted femoral hip joint prosthesis 10 after an extended period, say ten years, following implantation. As can be seen there has occurred a small amount of radiological subsidence, on the average of 2 mm, where the stem 11 has subsided within the integral unitary cement mantle formed from the preapplied cement mantle 29 becoming joined with the cement mantle 22. As may be seen in FIG. 6, such subsidence within the cement mantle results in the distal end 12 moving further into the centralizer 24 and in the enlarged shoulder 16 pulling away from the integral unitary cement mantle, including that portion formed from the preapplied cement mantle 29, thus leaving a gap 27. Because of the tapered-stem, collarless design of Co-Cr-Mo alloy having a highly polished surface, the femoral hip joint prosthesis 10 of the present invention is permitted to subside within the cement mantle 22 but to do so without disrupting the cement-bone interface. Thus, the subsidence of the stem 11 results in microscopic movement of the stem 11 in relation to the adjacent surface of the integral unitary cement mantle. As will be appreciated and as shown schematically in FIG. 6, the effect of such microscopic movement is to cause the stem 11 to self-tighten as it and the integral unitary cement mantle subside and to impart primarily compressive forces against the integral unitary cement mantle in directions substantially normal to the interior surfaces of the bone 20. This is illustrated schematically by the arrows 36 in FIG. 6.

In view of the fact that the preapplied cement mantle did not cover the distal end 12 of the stem 11 and the area adjacent thereto, any such subsidence will permit the distal end 12 to move freely into the centralizer 24. Thus, the distance from the distal end 12 to the beginning of the preapplied cement mantle 29 should be sufficiently great to accomodate the maximum expected subsidence of the stem 11 within the cement mantle and movement of the distal end 12 in the centralizer 24 without interference between the preapplied cement mantle 29 and the centralizer 24.

The hip joint prosthesis 10 shown in FIGS. 5 and 6 incorporates a modification in that the dimple 17' is drilled to a deeper depth than the dimple 17 of FIGS. 1 and 2 and is tapped to form internal threads 32. The threaded dimple 17' may then serve the dual function of assisting with insertion of the hip joint prosthesis 10, and the event replacement is required, with its removal. As can be seen from FIGS. 5 and 6, with this modification, no hole is provided in the shoulder 16. As will be appreciated, a tool (not shown) engages the threads 32 to assist in such insertion or removal.

Referring now to FIGS. 7–11, there is provided a modified femoral hip prosthesis 50 having a stem 51 which is convergently tapered toward the distal end 52 and extending along a first axis of symmetry C to an area of juncture with a neck portion 53 lying on a second axis of symmetry D. Extending from the neck portion 53 is a frustoconically-shaped Morse Taper Neck 54 to which may be attached a spherically-shaped Morse Taper Head. As in the previous embodiments, no collar is provided in the femoral hip prosthesis 50, but rather the portion of the prosthesis joining the stem 51 to the neck 53 follows a smooth arcuate contour in the area 55 of the included angle between the respective axes of symmetry C and D. The portion of the femoral hip prosthesis 50 opposite the smooth arcuate portion 55, namely, that portion on the outside of the angle between the two axes of symmetry C and D has an enlarged shoulder 56. As may be seen in FIG. 7, in profile the shoulder 56 includes a lower portion 57 which follows a straight line path aligned with the straight line path followed by the stem 51 and an upper portion 58 which follows a smooth, slightly curved path merging with the neck portion 53.

Figure 8:
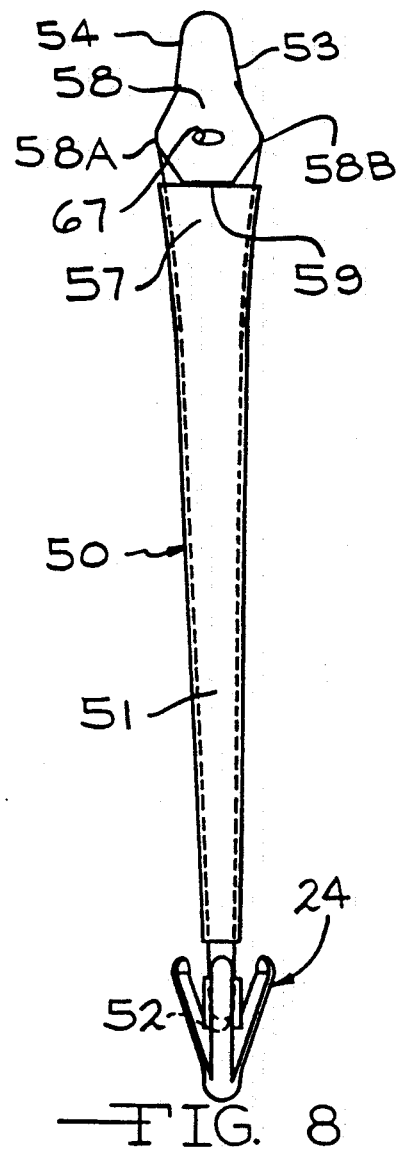
FIG. 8 is an end view of the femoral hip joint prosthesis of FIG. 7.

As may be seen from FIG. 8, the upper portion of the shoulder 58 follows a straight line path from one edge 58A to the opposite edge 58B. The area of juncture between the lower portion 57 and upper portion 58 provides a sharp line of demarcation 59 at the outermost portion of the shoulder 56.

Figure 7:
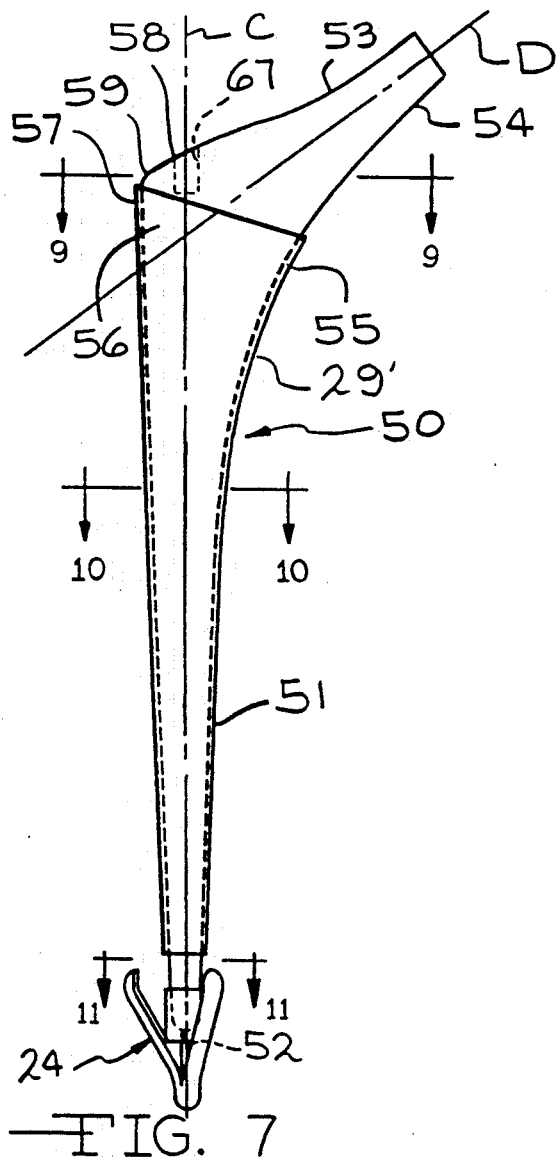
FIG. 7 is a front elevational view of another embodiment of the femoral hip joint prosthesis according to the present invention.

As may be seen in FIG. 7, the stem 51 diverges away from the axis C as it extends from the distal end 52 toward the shoulder 56. As may be seen from FIGS. 11 and 10, the stem 51 has a circular cross-sectional configuration near the distal end 52 and an oval configuration in the area approaching the arcuate area 55 and the shoulder 56 with the areas therebetween merging between circular and oval.

Figure 9:
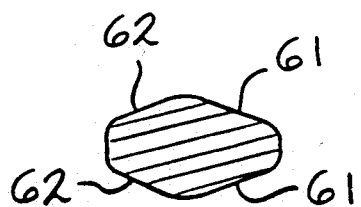
FIG. 9 is a sectional view taken through line 9—9 of FIG. 7.
Figure 10:
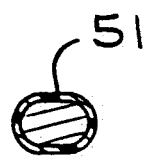
FIG. 10 is a sectional view taken through line 10—10 of FIG. 7.
Figure 11:
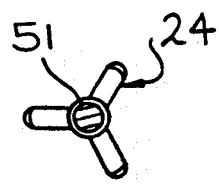
FIG. 11 is a sectional view taken through line 11—11 of FIG. 7.

Additionally, as may be seen in FIG. 9, the cross-sectional configuration in the area through the neck 53 and upper portion 58 of the shoulder 56 has a generally oval configuration with flattened segments 61 and 62 on opposite sides. Other cross-sectional configurations may be utilized in this area provided it merges smoothly with the stem 51 and the neck 53.

As in the previous embodiment, there is provided a preapplied cement mantle 29' of PMMA or other commercially available bone cement which encapsulates the stem 51 from a point approximately one (1) centimeter up from its distal end 52 to area near the line of demarcation 59 on the outside of the angle between the two axes of symmetry C and D and to an area on the arcuate contour 55 furthest spaced from such line of demarcation. As in the previous embodiment, a hollow centralizer 24 is provided in which the distal end 52 is inserted.

Also as in the previous embodiment, the upper portion 58 of the shoulder 56 may have formed therein a dimple or recess 67 which may, if desired, have internal threads (not shown). As in the previous embodiment, the dimple 67 is located on the first axis of symmetry C.

Figure 12:
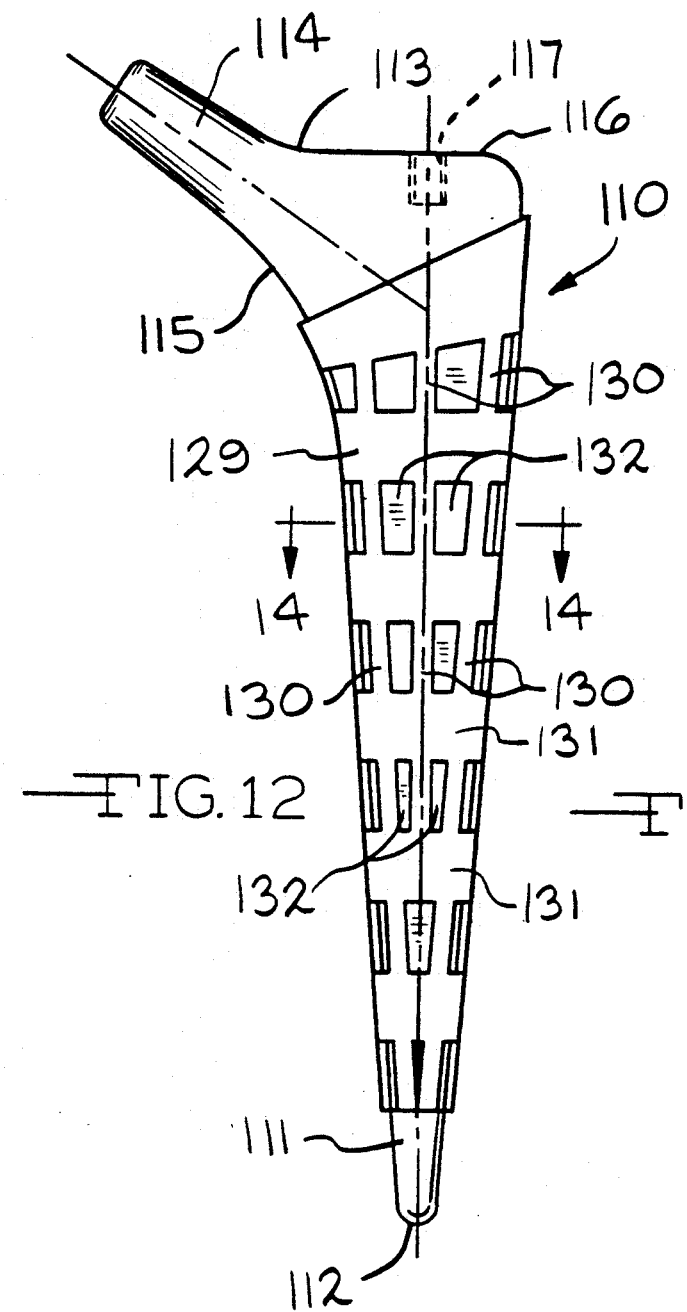
FIG. 12 is a front elevational view of a modified femoral hip joint prosthesis according to the present invention.
Figure 13:
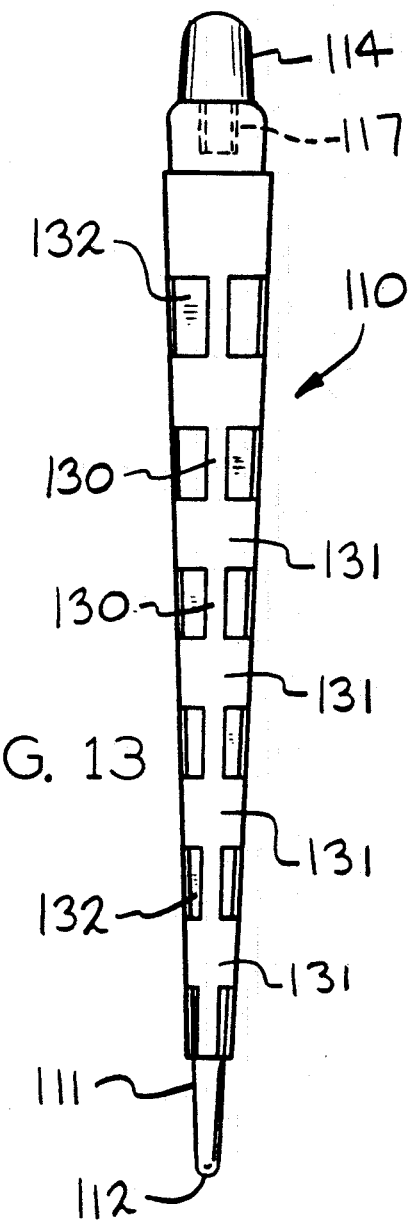
FIG. 13 is an end view of such modified femoral hip joint prosthesis.
Figure 14:
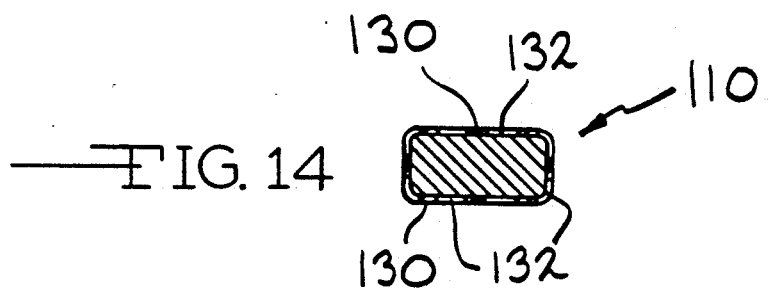
FIG. 14 is a sectional view taken through line 14—14 of FIG. 12.

Referring now to FIG. 12–14 there is shown another embodiment in which the preapplied cement mantle has an intermittent configuration. Under this embodiment there is provided a femoral hip joint prosthesis 110 having a stem 111 which is convergently tapered toward a distal end 112 and extending along a first axis of symmetry A' to an area of juncture with a neck portion 113 lying on a second axis of symmetry B'. Extending from the neck portion 113 is a frustoconically-shaped Morse Taper Neck 114 to which may be a spherically-shaped Morse Taper Head. As in the previous embodiment, no collar is provided in the femoral hip prosthesis, but rather the portion of the prosthesis joining the stem 111 to the neck 113 follows a smooth arcuate contour in area 115 of the included angle between the respective axes of symmetry A' and B'. The portion of the femoral hip prosthesis opposite the smooth arcuate portion 115, namely, that portion on the outside of the angle between the two axes of symmetry A' and B' as an enlarged shoulder 116 in which is formed a dimple or recess 117 for driving the prosthesis into the femur. As in the previous embodiments, the stem 111 is tapered in both directions. It may have the generally rectangular cross-section configuration such as that shown in the embodiment of FIGS. 1–4 and 12–14 or a circular cross-sectional configuration or one which has a portion with a circular cross-sectional configuration and other sections with a generally oval configuration similar to that disclosed in the embodiment of FIGS. 7–11.

The femoral hip joint prosthesis further includes a preapplied cement mantle 129 of PMMA or other commercially available bone cement. Under this embodiment the preapplied cement mantle 129 is placed intermittently on the stem 111 and encapsulates only a portion of the stem 111. Preferably, the preapplied cement mantle 129 extends in intermittent fashion from a point adjacent the distal end 112 or slightly upwardly therefrom to a point on the stem 111 near the beginning of such enlarged shoulder 116.

As can be seen in FIGS. 12–14, the preapplied cement mantle 129 has a series of spaced apart longitudinal rib members 130 extending generally parallel to the axis A' and a series of transverse or circumferential rib members 131 extending circumferentially around the stem 111 in spaced apart manner and joining the longitudinal rib members 130. Since the longitudinal rib members 130 are spaced apart from each other and the circumferential rib members 131 are spaced apart from each other, they will cooperate to define a series of interstices 132 through which the surface of the stem 111 will be visible.

Although the preapplied cement mantle 129 of this embodiment is shown as having a series of longitudinal rib members 130 and a series of circumferential members 131 defining the interstices 132, it should be understood that the preapplied cement mantle 129 may be of any desired pattern and have interstices 132 of any desired pattern therebetween. Thus, for example, the preapplied cement mantle 129 could cover a greater portion of the surface of the stem 111 and simply have circular or other shaped interstices or a lesser portion.

Under this embodiment, it will be appreciated that upon insertion of the stem 111 in a prepared intramedullary canal having cement deposited therein, the fresh cement will flow into the interstices 132 to make contact with the polished surface of the stem 111 and will also encapsulate the longitudinal and circumferential rib members 130 and 131 to form a unitary mantle around the stem 111. As will be appreciated, a portion of the new cement mantle aligned with the interstices will be thicker than the new cement mantle covering the longitudinal and circumferential rib members 130 and 131. However, as with the previous embodiment, the stem 111 will be able to subside within the cement mantle, both those portions of the metal stem 111 surface contacted by the longitudinal and circumferential rib portions 130 and 131 of the preapplied cement mantle 129 and those portions aligned with the interstices 132 which are contacted by the new cement placed in the intramedullary canal preparatory to insertion of the stem 111 therein.

The present invention of a femoral hip joint prosthesis, having a highly polished surface, collarless and a tapered stem, permits patients to enjoy long lasting and predictable results.

Modifications will be readily apparent to those skilled in the art. Accordingly, the present invention should be limited only by the scope of the claims.

We claim:

1. A femoral hip joint prosthesis for insertion into a prepared intramedullary canal with cement comprising in combination (1) a structural member formed of metal and having an elongated stem extending from a proximal end to a distal end, said stem tapering from larger to progressively smaller cross-sectional sizes from said proximal end to said distal end;
    said stem having an uninterrupted surface with a polished finish and (2) a preapplied cement mantle on said stem, said preapplied cement mantle extending intermittently from a lower end adjacent said distal end toward said area of juncture and providing an interface with said stem which permits subsidence of the stem therein upon application of loads toward said distal end such subsidence causing said stem to self-tighten therein.

2. A femoral hip joint prosthesis according to claim 1, wherein said lower end of said cement mantle is spaced from said distal end by a distance of at least 0.5 cm.

3. A femoral hip joint prosthesis according to claim 1, wherein said preapplied cement mantle has a series of interruptions extending through its full thickness, said stem being visible at said interruptions.

4. A femoral hip joint prosthesis according to claim 1, wherein said preapplied cement mantle has a substantially uniform thickness in the range of 0.75 to 2 mm.

5. A femoral hip joint prosthesis for insertion into a prepared intramedullary canal with cement forming an interfacial bond with said intramedullary canal comprising in combination (1) a structural member formed of metal and having an elongated stem extending from a proximal end to a distal end and defining a first axis, said proximal end having a neck region which joins the stem at a juncture, said stem having anterior, posterior, medial and lateral surfaces and said surfaces tapering downwardly from said juncture to said distal end;
    said neck region defining a second axis disposed at an obtuse angle with the first axis, and
    said medial surface defining a smooth arcuate path from the stem across the juncture to the neck region and said lateral surface defining an enlarged shoulder proximal said juncture; and
    said surfaces of said stem being uninterrupted and having a polished finish throughout and (2) a preapplied cement mantle on said stem, said preapplied cement mantle extending intermittently from a lower end adjacent said distal end toward said area of juncture and providing an interface with said stem which permits subsidence of the stem therein upon application of loads toward said distal end such subsidence causing said stem to self-tighten therein without disrupting said interfacial bond.

6. A femoral hip joint prosthesis for insertion into a prepared intramedullary canal with cement comprising in combination (1) a structural member formed of metal and having an elongated stem extending from a proximal end to a distal end, said stem tapering from larger to progressively smaller cross-section sizes from said proximal end to said distal end, said stem having an uninterrupted surface with a polished finish and (2) a preapplied cement mantle on said stem extending intermittently throughout a major portion of said stem, said preapplied cement mantle having a substantially uniform thickness and defining a series of interstices extending through said thickness to said polished finish.

7. A femoral hip joint prosthesis according to claim 6, wherein said preapplied cement mantle extends intermittently from a lower end spaced from said distal end by a distance of 0.5 to 1.5 cm to said proximal end.

8. A femoral hip joint prosthesis according to claim 6, wherein said preapplied cement mantle has a thickness in the range 0.75 to 2 mm.

9. A femoral hip joint prosthesis according to claim 6, in combination with a centralizer having a pocket with an open upper end and a lower end, said distal end positioned in said pocket and spaced from said lower end, said preapplied cement mantle having a lower end spaced upwardly from said centralizer upper end by distance at least equal to the distance between said distal end and said centralizer lower end.

10. A femoral hip joint prosthesis comprising (1) a structural member formed of metal and having an elongated stem extending from a proximal end to a distal end, said stem tapering from larger to progressively smaller cross-sectional sizes from said proximal end to said distal end, said stem having uninterrupted surfaces with a polished finish and (2) a preapplied cement mantle on said surfaces, said preapplied cement mantle extending intermittently throughout a major portion of said stem and providing an interface with said stem which permits subsidence of the stem therein upon application of loads toward said distal end such subsidence causing said stem to self-tighten therein.

11. A femoral hip joint prosthesis according to claim 10, wherein said preapplied cement mantle extends intermittently from a lower end spaced from said distal end by a distance of 0.5 to 1.5 cm to said proximal end.

12. A femoral hip joint prosthesis according to claim 10, wherein said preapplied cement mantle has a thickness in the range of 0.75 to 2 mm.

13. A femoral hip joint prosthesis comprising (1) a structural member formed of metal and having an elongated stem extending from a proximal end to a distal end, said stem having surfaces with a polished finish and (2) a preapplied cement mantle on said surfaces, said preapplied cement mantle extending intermittently throughout a major portion of said stem.

14. A femoral hip joint prosthesis according to claim 13, wherein said preapplied cement mantle extends intermittently from a lower end spaced from said distal end by a distance of 0.5 to 1.5 cm to said proximal end.

15. A femoral hip joint prosthesis according to claim 13, wherein said preapplied cement mantle has a thickness in the range of 0.75 to 2 mm.

* * * * *